United States Patent [19]
Schild et al.

[11] Patent Number: 5,435,009
[45] Date of Patent: Jul. 25, 1995

[54] INFLATABLE COMPRESSION GARMENT

[75] Inventors: Rolf Schild, London; Brian Hawkins, Bedfordshire, both of England

[73] Assignee: Huntleigh Technology PLC, Bedfordshire, United Kingdom

[21] Appl. No.: 121,421

[22] Filed: Sep. 16, 1993

[30] Foreign Application Priority Data

Oct. 1, 1992 [GB] United Kingdom ............... 9220716

[51] Int. Cl.⁶ .................... A41D 13/06; A61F 13/06
[52] U.S. Cl. ...................................... 2/22; 2/DIG. 3; 602/13; 602/27; 128/DIG. 20
[58] Field of Search ............... 2/2, 239, DIG. 3, 22, 2/24, 242, 267; 602/13, 27; 606/201; 128/DIG. 20; 36/29, 153, 154

[56] References Cited

U.S. PATENT DOCUMENTS

| | | | |
|---|---|---|---|
| 2,450,862 | 10/1948 | Wilkinson | 602/27 |
| 3,351,055 | 11/1967 | Gottfried | 128/DIG. 20 |
| 4,722,332 | 2/1988 | Saggers | 128/DIG. 20 |
| 4,730,610 | 3/1988 | Graebe | 128/DIG. 20 |
| 5,113,599 | 5/1992 | Cohen et al. | 36/29 |
| 5,277,695 | 1/1994 | Johnson, Jr. et al. | 128/DIG. 20 |

FOREIGN PATENT DOCUMENTS 8503219 8/1985 WIPO.
9200715 1/1992 WIPO.

*Primary Examiner*—Clifford D. Crowder
*Assistant Examiner*—Amy B. Vanatta
*Attorney, Agent, or Firm*—Fitzpatrick, Cella, Harper & Scinto

[57] ABSTRACT

An inflatable garment applies compression to a limb for the treatment of vascular disorders. The garment is made with an inflatable chamber formed from a blank of superimposed layers of sheet material. Side portions of the blank are joined together in the garment to encompass the foot. An inflatable tongue is located to lie under the foot. The side portions of the blank and the tongue form intercommunicating inflatable sacs. The tongue itself is not laterally joined to the side portions of the blank. The resulting inflatable garment is more comfortable to wear and more effective therapeutically.

9 Claims, 3 Drawing Sheets

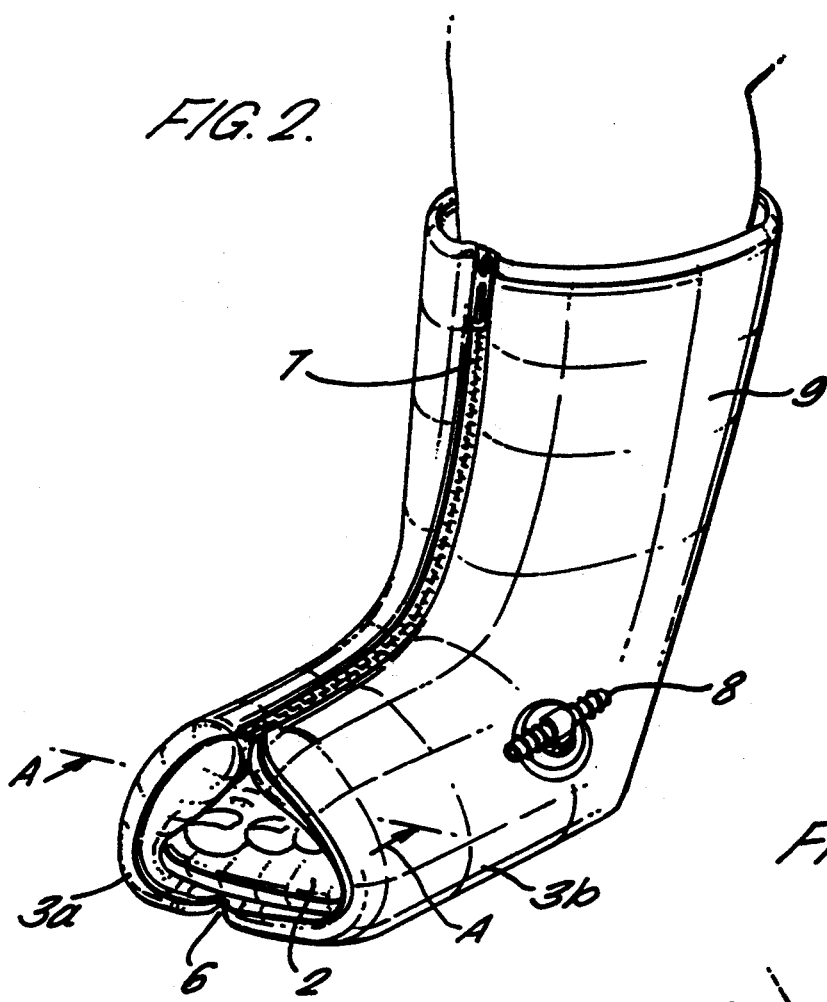
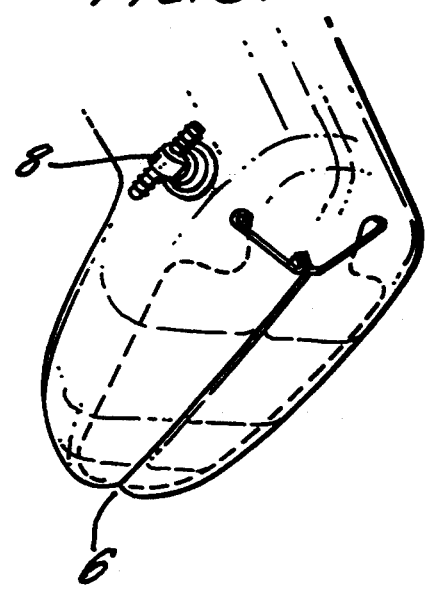
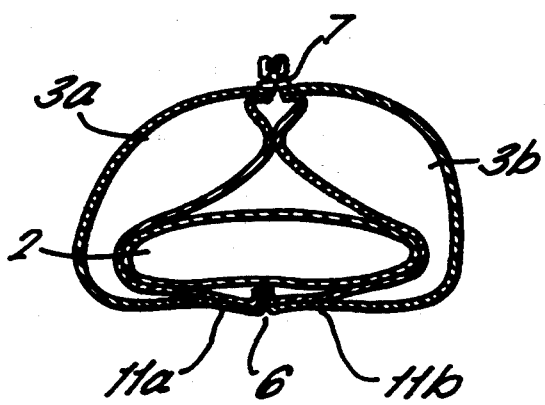

INFLATABLE COMPRESSION GARMENT

BACKGROUND OF THE INVENTION

1. Field of the Invention

The present invention relates to inflatable garments, in particular, inflatable garments which can apply compression to a limb in order to treat vascular disorders and edemas and for general therapeutic treatment.

2. Description of the Prior Art

Compression garments, particularly to give intermittent compression, which enclose the foot and lower leg of a patent are well known. Such a garment is described in WO 92/00715. This garment has a single seam running under the sole of the foot, and a zip running over the upper part of the foot and up the front of the leg. The single seam results in pressure being applied to the sides of the foot rather than being evenly distributed around the foot. This can cause toe pinching and discomfort to the patient, particularly at higher pressures. The phenomenon of toe pinching is substantially overcome in a garment such as described in WO 85/03219 which comprises two seams running under the sole of the foot and a zip running over the upper part of the foot and up the front of the leg. The two seams join three inflated sacs, one below the foot and one on either side of the foot, the side sacs being joined by the zip. There are certain disadvantages with this arrangement in that, whilst the pressure is more evenly distributed, the two seams are able to contact the foot and cause discomfort and there is virtually no pressure applied to certain areas of the foot, in particular, the instep and near the heel.

SUMMARY OF INVENTION

According to the present invention there is provided an inflatable garment for applying compression to the foot of a patient, comprising an inflatable chamber formed from a blank of superimposed layers of sheet material, the blank having side portions which are laterally joined together in the garment to encompass the foot, and an inflatable tongue located to lie under the sole of the foot, the side portions and the tongue forming intercommunicating inflatable sacs, wherein the tongue is not laterally joined to the side portions. With this arrangement the shape and size of the inflatable tongue can be selected as required to ensure adequate pressure support under the entire sole of the foot including the heel.

Conveniently the tongue is formed as a portion of the blank. Instead, however, the tongue may be separate from the blank and the garment may then include a length of tube interconnecting the tongue and said chamber. Preferably, the side portions of the blank are laterally joined together beneath the tongue. Then the garment may include a non-inflatable web of sheet material interconnecting the side portions beneath the tongue. This web may be formed from at least one layer of the blank.

In a preferred embodiment, the tongue is wider than said web between the side portions.

Clearly, although the garment may apply pressure only around the foot region, it is very preferable for said chamber to be adapted to apply pressure to the lower leg as well.

BRIEF DESCRIPTION OF THE DRAWINGS

A preferred embodiment of the present invention will now be described in detail, by way of example only, with reference to the accompanying drawings, of which:

FIG. 2 depicts in perspective, the garment in FIG. 1 when assembled and, in use, on a patient's lower leg and foot;

FIG. 3 is a view from below, of the garment in FIG. 2;

FIG. 4 is a cross sectional view taken in direction A—A in FIG. 2; and

DETAILED DESCRIPTION OF THE PREFERRED EMBODIMENT

Figure 1:
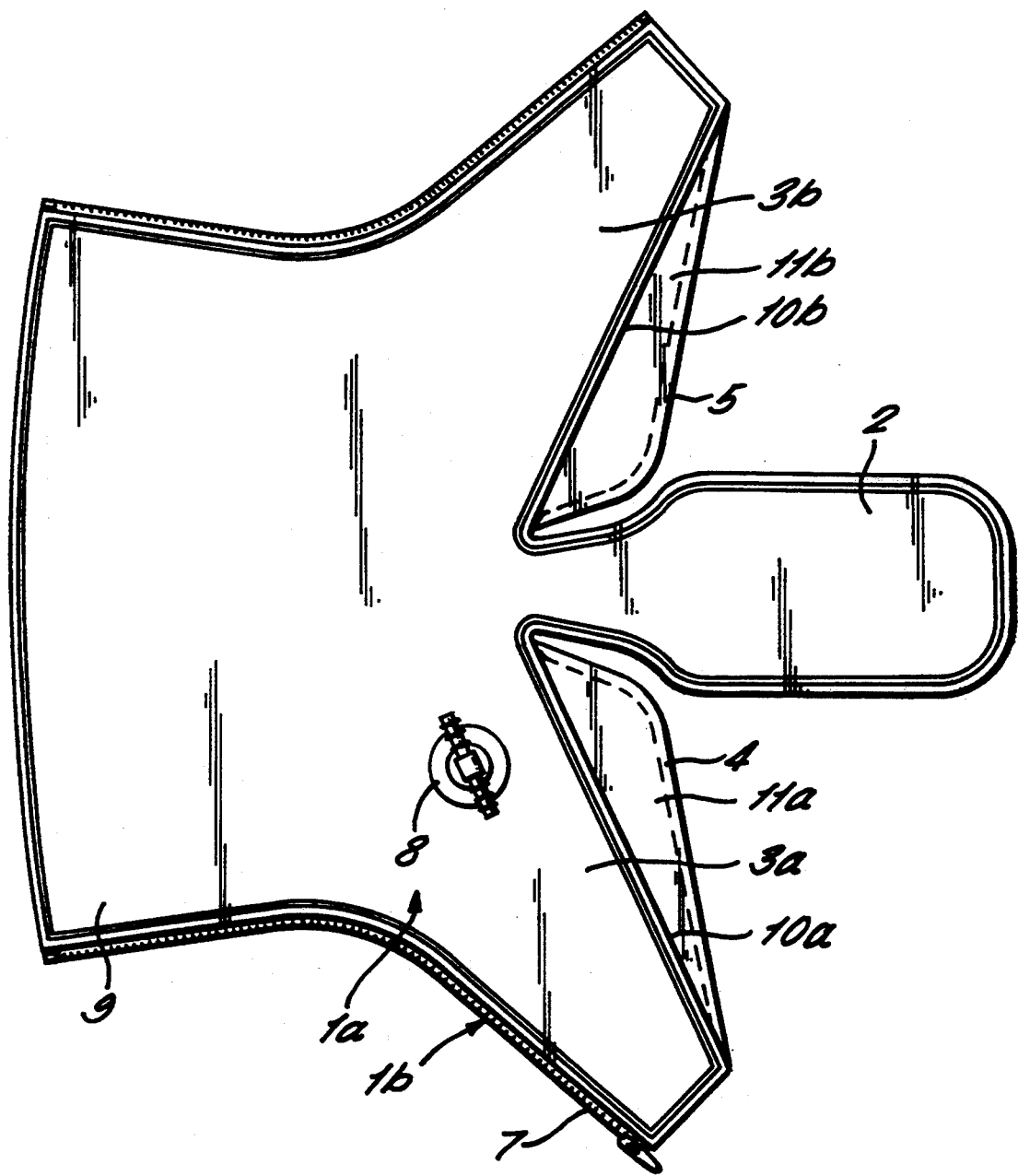
FIG. 1 depicts, in plan view, a material blank for use in constructing the inflatable garment.

FIG. 1 shows the blank comprising a pair of superimposed sheets 1a, 1b, from which the inflatable garment is made. The sheets 1a, 1b are secured together around their periphery by high frequency welding, for example, to form an inflatable chamber. The blank formed by the sheets 1a, 1b has an inflatable tongue portion 2 and two inflatable side portions 3a, 3b. In this embodiment additional weld lines 10a and 10b seal the two sheets 1a and 1b together along the side portions 3a and 3b, to leave non-inflatable web portions 11a and 11b along the edges of the side portions adjacent the tongue portion 2.

When the blank is used to form the inflatable garment, the peripheral edges of these web portions 11a and 11b are stitched together, or otherwise seamed, along lines 4 and 5 to provide a sole for the inflatable garment (or boot). The tongue portion 2 remains separate from the side portions 3a and 3b so that, in use, it rests above the seam 6 where the side portions are stitched together (see FIG. 2). The garment is located and secured on the lower leg and foot by means of a zipper fastener 7 which runs over the upper part of the foot and up the front of the lower leg.

The garment is inflated by attaching a source of inflation fluid to an inlet 8 whereby inflation fluid can fill the chamber formed by the blank including the tongue portion 2, side portions 3a and 3b and leg portion 9.

FIG. 2 depicts clearly how the tongue portion 2 which lies directly below the foot prevents the seam 6 from contacting the sole of the foot thereby preventing any discomfort to the patient.

FIG. 3 is a view from below of the garment in FIG. 2 where the single seam 6 can be clearly seen.

FIG. 4 is a cross sectional view taken in direction A—A in FIG. 2. This figure depicts the uninflated region formed by the web portions 11a and 11b. The tongue portion 2 is made sufficiently wide to cover this region thereby ensuring that the foot is sufficiently supported and distanced from seam 6. In this way, a substantially equal pressure can be applied to the entire foot.

In the illustrated example, the tongue portion is made wider than the uninflated region so that the tongue and side portions between them apply pressure all round the foot leaving no substantial dead areas where no or inadequate pressure is applied. In particular, there is no tendency for the side edges of the foot to come into contact with side seams as posssible in the prior art arrangement, and the tongue portion can be formed to be wide enough near the heel of the patient to ensure all round pressure is applied.

Indeed the shape of the tongue portion can be selected and controlled to provide a desired degree of pressure over all areas of the sole of the patient's foot. For example, the tongue may be made wider or larger in the arch region of the foot to provide required pressure in this area. Also the shape of the tongue portion can be selected to accommodate different foot sizes.

Furthermore, it is envisaged that the garment could also comprise an inflatable upper portion which, in use, will rest above the foot where the zipper fastener 7 would normally contact the foot. In this way, the foot can be protected from contact by the zipper fastener and the foot receives a further improved evenness of compression over its entire surface.

Figure 5:
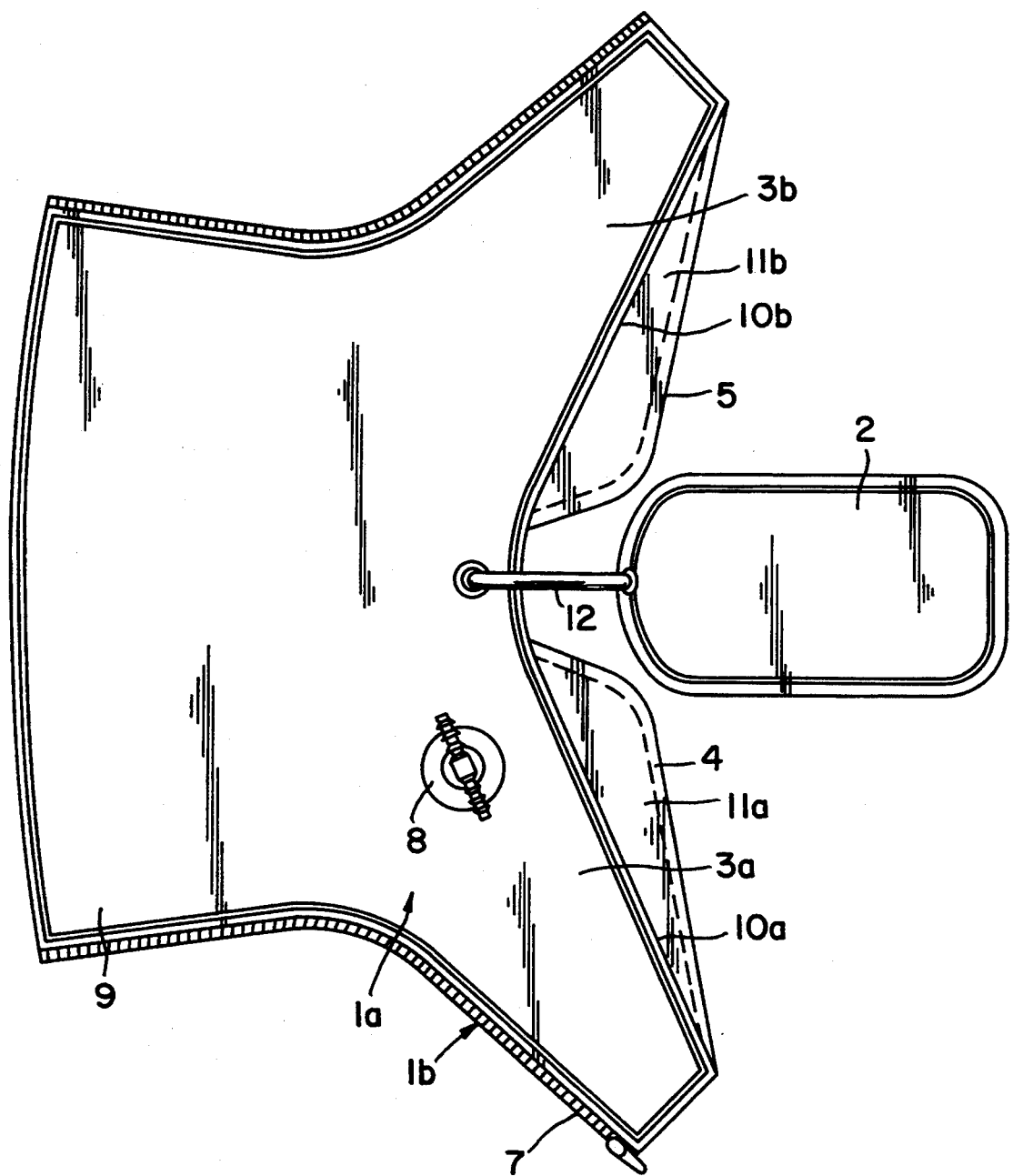
FIG. 5 depicts, in plan view, a blank for a further embodiment of the invention.

Further modifications of the above described embodiment are possible. For example, as shown in FIG. 5 the tongue portion 2 may be formed as a separate chamber and connected to the main chamber by a length of tube 12.

What is claimed is:

1. An inflatable garment for applying compression to the foot of a patient, comprising:
    an inflatable chamber formed from a blank of superimposed layers of sheet material, said blank having first and second side portions which are laterally joined together to form a seam when the garment is closed to encompass the foot; and
    an inflatable tongue extending from said blank and located to lie under the sole of the foot and over said seam, said side portions and said tongue forming intercommunicating inflatable sacs, wherein said tongue is not laterally joined to said side portions.

2. An inflatable garment as claimed in claim 1, wherein said tongue is formed as a portion of the blank.

3. An inflatable garment as claimed in claim 1, wherein said tongue is separate from said blank and the garment includes a length of tube interconnecting said tongue and said chamber.

4. An inflatable garment as claimed in claim 1, wherein said side portions of said blank are laterally joined together beneath the tongue.

5. An inflatable garment as claimed in claim 4, further including a non-inflatable web of sheet material interconnecting said side portions beneath said tongue.

6. An inflatable garment as claimed in claim 5, wherein said web is formed from at least one layer of the blank.

7. An inflatable garment as claimed in claim 5, wherein said tongue is wider than said web between said side portions.

8. An inflatable garment as claimed in claim 1, wherein said chamber is adapted to apply pressure to the foot and lower leg of a patient.

9. An inflatable garment for applying compression to a limb of a patient, comprising:
    an inflatable chamber formed from a blank of superimposed layers of sheet material, said blank having first and second lateral side portions;
    means for enclosing said inflatable chamber on all lateral sides, wherein when said inflatable chamber is closed said first and second lateral portions are disposed next to each other to form a seam; and
    an inflatable tongue extending from said blank to cover a top portion of said seam and an interior surface of said enclosed inflatable chamber.

* * * * *